US00PP21312P2

(12) United States Plant Patent
Baijens

(10) Patent No.: US PP21,312 P2
(45) Date of Patent: Sep. 21, 2010

(54) ***ECHINACEA* PLANT NAMED "KIECHOTPI"**

(50) Latin Name: ***Echinacea purpurea* (L) *Moench***
Varietal Denomination: Kiechotpi

(75) Inventor: Martijn Baijens, Grootebroek (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/459,715

(22) Filed: Jul. 7, 2009

(51) Int. Cl.
*A01H 5/00* (2006.01)

(52) U.S. Cl. ..... Plt./428

(58) Field of Classification Search ..... Plt./263, Plt./428
See application file for complete search history.

*Primary Examiner*—Susan B McCormick Ewoldt

(74) *Attorney, Agent, or Firm*—Jondle & Associates, P.C.

(57) ABSTRACT

An *Echinacea* cultivar particularly distinguished by its compact, upright, and V-shaped habit, numerous, medium-sized, hot-pink colored flowers, and good basal branching, is disclosed.

2 Drawing Sheets

Genus and species: *Echinacea purpurea* (L) *Moench.*
Variety denomination: 'Kiechotpi'.

BACKGROUND OF THE NEW PLANT

The present invention comprises a new and distinct cultivar of *Echinacea*, botanically known as *Echinacea purpurea* (L) *Moench*, and hereinafter referred to by the cultivar name 'Kiechotpi.' The new cultivar originated from a cross conducted in September 2003 in Venhuizen, The Netherlands, between the female parent, an unnamed seedling (unpatented), and the male parent, 'White Swan' (unpatented).

The new cultivar was first propagated in the summer of 2006 in Steenbergen, The Netherlands, and has been asexually reproduced repeatedly by in-vitro propagation and cuttings, over a three-year period. The present invention has been found to retain its distinctive characteristics through successive asexual propagations.

SUMMARY OF THE INVENTION

The following are the most outstanding and distinguishing characteristics of the new cultivar when grown under normal horticultural practices in Venhuizen, The Netherlands.

1. A compact, upright, and V-shaped habit;
2. Hot-pink colored flowers;
3. Numerous, medium-sized flowers; and
4. Good basal branching.

DESCRIPTION OF THE PHOTOGRAPHS

This new *Echinacea* plant is illustrated by the accompanying photographs which show overall plant habit including inflorescences, buds, and foliage of the plant. The colors shown are as true as can be reasonably obtained by conventional photographic procedures. The photos are of a 4 month-old plant grown in a 12.0 cm to 14.0 cm container in a greenhouse in the summer in Venhuizen, The Netherlands.

DESCRIPTION OF THE NEW CULTIVAR

Figure 1:
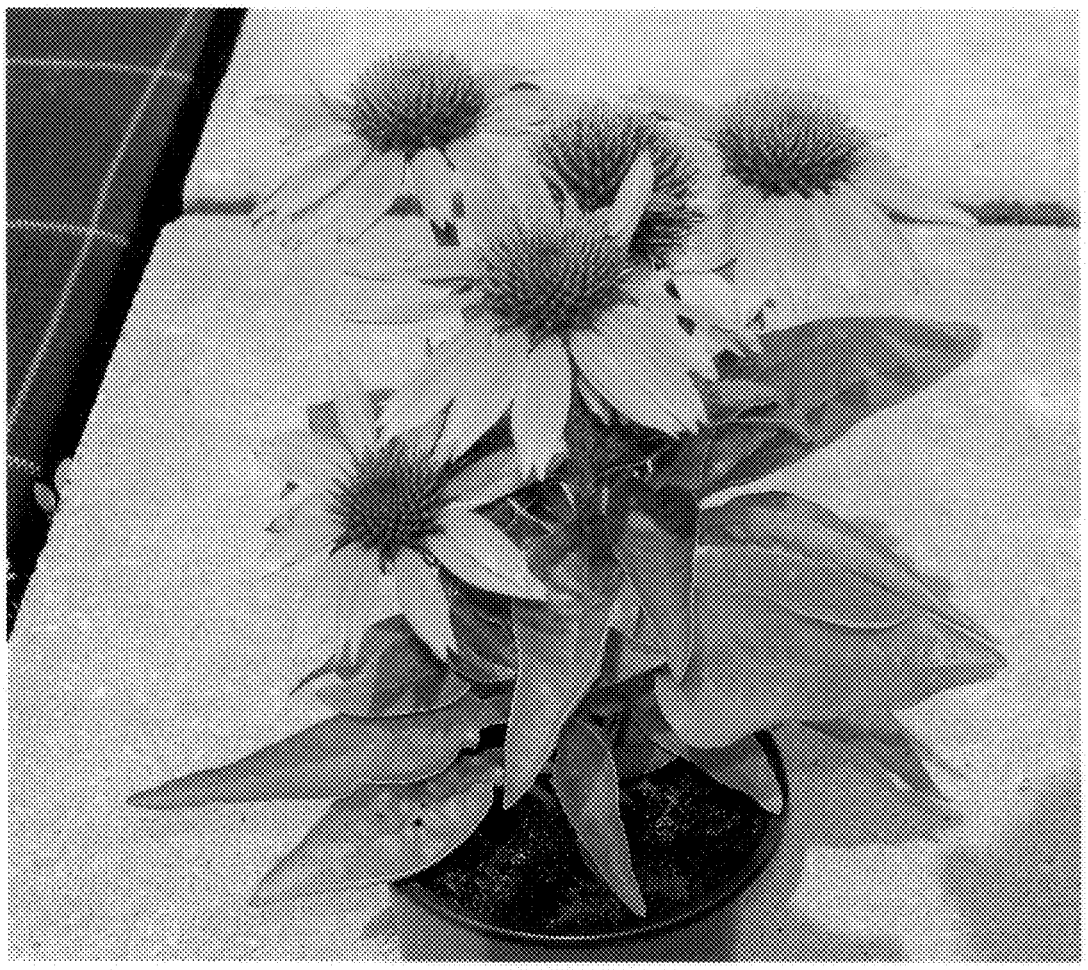
FIG. 1 shows the overall plant habit including inflorescences and foliage.
Figure 2:
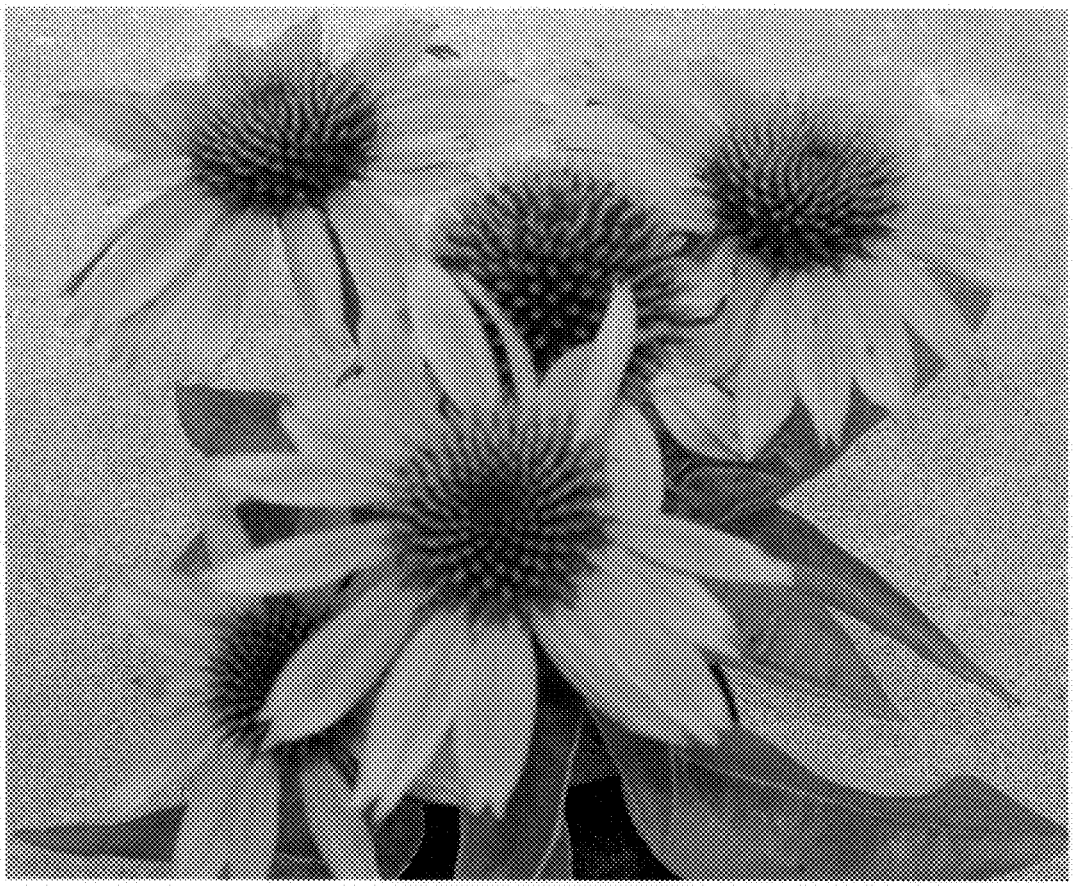
FIG. 2 shows a closer view of the inflorescences.

The following detailed descriptions set forth the distinctive characteristics of 'Kiechotpi.' The data which define these characteristics were collected from asexual reproductions carried out in Venhuizen, The Netherlands. The plant history was taken on 4 month old, un-pinched plants grown in 12.0 cm to 14.0 cm pots in a greenhouse in the summer. The color readings were determined under natural light. Color references are to The R.H.S. Colour Chart of The Royal Horticultural Society of London (R.H.S.) (1986).

DESCRIPTION OF THE NEW PLANT

Classification:
- *Family.*—Asteraceae.
- *Botanical name*—*Echinacea purpurea* (L) *Moench.*
- *Common name.*—Coneflower, *echinacea.*

Parentage:
- *Female parent.*—An unnamed *Echinacea purpurea* (L) *Moench* seedling.
- *Male parent.*—'White Swan' (unpatented).

Plant:
- *Form and habit.*—Compact, upright, V-shaped habit; bushy, well-branched.
- *Growth and branching habit.*—Basal branching.
- *Height (from top of soil, including inflorescences).*—25.0 cm to 30.0 cm.
- *Width.*—15.0 cm to 20.0 cm.
- *Vigor.*—Strong.
- *Time to produce a finished flowering plant.*—8 weeks (June) or 12 weeks (April) from a 72-cell plug to an 8-inch pot.
- *Outdoor plant performance.*—Very strong; good tolerance to wind, rain, and heat.
- *Time to initiate and develop roots.*—6 weeks (from Agar) to a 72-cell liner.
- *Root description.*—Many white, fibrous roots; some thick and fleshy main roots.

Stems:
*Branching.*—V-shaped plant silhouette.
*Total number of branches.*—10 to 16.
*Length.*—5.0 cm to 12.0 cm.
*Diameter.*—0.5 cm to 0.8 cm.
*Internode length.*—1.0 cm to 3.0 cm.
*Appearance.*—Round and green-red.
*Strength.*—Strong.
*Color.*—About RHS 200C.
*Texture.*—Pubescence: Present. Length of hairs: 0.1 cm. Color of hairs: Lighter than RHS 145D.

Leaves:
*Arrangement.*—Basal leaves are opposite and after flowering become alternate.
*Shape.*—Lanceolate.
*Apex.*—Acute.
*Base.*—Alternate.
*Margin.*—Entire.
*Size.*—Length: 5.0 cm to 8.0 cm. Width: 1.0 cm to 4.0 cm.
*Immature and mature leaf.*—Color: Upper surface: RHS 137A and RHS 137B. Lower surface: RHS 137C and RHS 137D.
*Pubescence* (*both surfaces*).—Present. Length of hairs: 0.1 cm. Color of hairs: About RHS 200C.
*Venation.*—Linear.
*Vein color.*—Upper surface: RHS 137C. Lower surface: RHS 137D.

Petioles:
*Length.*—1.0 cm to 7.0 cm.
*Diameter.*—0.2 cm to 0.3 cm.
*Color* (*both surfaces*).—RHS 137D.
*Texture* (*both surfaces*).—Pubescence: Present. Length of hairs: 0.1 cm. Color of hairs: About RHS 200C.

Inflorescence buds:
*Shape.*—Ovoid, conical.
*Length.*—1.0 cm.
*Diameter.*—1.0 cm.
*Color.*—RHS 137A.

Inflorescence:
*Type.*—Capitulum.
*Arrangement.*—Terminal capitulum consisting of numerous disc florets, one row of ray florets and three rows of involucral bracts.
*Blooming habit.*—From late spring into autumn.
*Quantity of open inflorescences per stem.*—3 to 7.
*Quantity of buds per stem.*—2 to 6.
*Quantity of open inflorescences and buds per plant.*—10 to 25.
*Rate of inflorescence opening.*—1 per 1 to 2 days.
*Lastingness of the inflorescences on the plant.*—2 to 3 weeks.
*Fragrance.*—Absent.
*Inflorescence size.*—Height: 1.0 cm to 2.0 cm (excluding peduncle). Diameter: 8.0 cm to 10.0 cm.
*Disc diameter.*—2.0 cm to 3.0 cm.
*Persistent or self-cleaning.*—Self-cleaning.

Disc floret:
*Arrangement.*—Spirally placed on the disc.
*Quantity per inflorescence.*—About 400.
*Shape.*—Star-shaped.
*Apex.*—Pointed.
*Base.*—Rounded.
*Margin.*—Entire.
*Size.*—Length: 0.4 cm to 0.6 cm. Diameter: 0.1 cm.
*Texture* (*both surfaces*).—Pubescent.
*Color, when opening* (*both surfaces*).—RHS 23A and RHS 150A.
*Color, when fully opened* (*both surfaces*).—RHS 23A and RHS 46A.

Ray floret:
*Arrangement.*—Rotate.
*Quantity per inflorescence.*—20 to 34.
*Number of whorls.*—1 to 2.
*Shape.*—Lanceolate.
*Apex.*—Notched.
*Base.*—Pointed.
*Margin.*—Entire.
*Texture.*—General: Smooth. Upper surface: Not pubescent. Lower surface: Some pubescence on veins.
*Size.*—Length: 3.0 cm to 5.0 cm. Width: 1.0 cm to 1.3 cm.
*Color, when opening.*—Upper surface: RHS 67A. Lower surface: About RHS 61 and white, lighter than RHS 150D.
*Color, when fully opened.*—Upper surface: RHS 67B. Lower surface: RHS 63C.
*Color, fading to.*—Upper surface: RHS 75B and RHS 75C. Lower surface: RHS 68B and RHS 68C.

Peduncle:
*Length, terminal peduncle.*—5.0 cm to 15.0 cm.
*Length, fourth peduncle.*—7.5 cm to 10.0 cm.
*Length, seventh peduncle.*—12.5 cm to 14.0 cm.
*Diameter.*—0.5 cm to 0.7 cm.
*Aspect/angle.*—45°.
*Strength.*—Fibrous and sturdy.
*Texture.*—Pubescence: Present. Length of hairs: 0.05 cm. Color of hairs: About RHS 200C.
*Color.*—RHS 139C.

Involucral bracts:
*Arrangement.*—Rotate, placed in three rows.
*Number of bracts per inflorescence.*—About 50.
*Shape.*—Lanceolate, curved towards the peduncle.
*Apex.*—Acute.
*Base.*—Cuneate.
*Margin.*—Entire.
*Texture* (*both surfaces*).—Pubescent. Length of hairs: 0.05 cm. Color of hairs: About RHS 200D.
*Size.*—Length: 0.8 cm. Width: 0.1 cm to 0.2 cm.
*Color* (*both surfaces*).—RHS 137.

Receptacle:
*Size.*—Height: About 1.2 cm. Diameter: About 1.5 cm.
*Spines.*—Number of spines per disc floret: 1. Appearance: Longer than disc florets. Apex: Sharp acuminate. Base: Blunt. Texture: Smooth. Color: Apex: RHS 23 and RHS 24. Mid-section: RHS 144C. Base: RHS 155D.

Reproductive organs:
*Androecium.*—Location: Present on disc florets only. Stamens: Number: 5 per floret. Filament length: 0.2 cm. Filament color: RHS 140A. Anther shape: Elongated oblong. Anther length: 0.1 cm. Anther color: RHS 202. Pollen color: RHS 15A. Pollen amount: Moderate.
*Gynoecium.*—Location: Present on ray and disc florets. Number: 1 per floret. Pistil length: 0.4 cm. Stigma color: RHS 200D. Stigma shape: Double. Style color: About RHS 6C. Style length: 0.1 cm. Ovary color: About RHS 200.

Fruit and seed set: Some seed set observed. The seeds are whitish, 0.2 cm long (typical composite style), and have a smooth surface.

Disease and insect resistance: Average/typical of the species.

COMPARISON WITH PARENTAL AND COMMERCIAL CULTIVARS

'Kiechotpi' differs from the female parent, an unnamed seedling (unpatented), in that 'Kiechotpi' has hot-pink colored flowers and a compact growth habit, while the unnamed seedling has pink flowers and a semi-compact growth habit.

'Kiechotpi' differs from the male parent, 'White Swan' (unpatented), in that 'Kiechotpi' has hot-pink colored flowers and a compact growth habit, while 'White Swan' has white flowers and a medium-high growth habit.

'Kiechotpi' differs from the cultivar 'Kim's Knee High' (U.S. Plant Pat. No. 12,242) in that 'Kiechotpi' has hot-pink colored flowers that retain their color, while 'Kim's Knee High' has soft pink flowers that fade with maturity. Additionally, 'Kiechotpi' has a better branching habit than 'Kim's Knee High'.

I claim:

1. A new and distinct cultivar of *Echinacea* plant as shown and described herein.

* * * * *